(12) United States Patent
Petit et al.

(10) Patent No.: US 6,251,937 B1
(45) Date of Patent: Jun. 26, 2001

(54) 5,6-0-ALKYLIDENE GLUCONO-1(4)-LACTONES AND DERIVATIVES, PROCESSES FOR THEIR PREPARATION AND USES THEREOF

(75) Inventors: Serge Petit, Cusy; Stephane Fouquay, Mont Saint-Aignan, both of (FR)

(73) Assignee: CECA S.A., Puteaux (FR)

( * ) Notice: Subject to any disclaimer, the term of this patent is extended or adjusted under 35 U.S.C. 154(b) by 0 days.

(21) Appl. No.: 09/058,983

(22) Filed: Apr. 13, 1998

(30) Foreign Application Priority Data

Apr. 11, 1997 (FR) .................................... 97 04471

(51) Int. Cl.$^7$ ...................... A61K 31/335; C07D 305/00
(52) U.S. Cl. ...................... 514/467; 549/314; 549/454
(58) Field of Search ...................... 549/454, 314; 514/467

(56) References Cited

U.S. PATENT DOCUMENTS 4,111,958   9/1978   Crawford .......................... 260/340.7

FOREIGN PATENT DOCUMENTS 0 506 235   9/1992   (EP) .

OTHER PUBLICATIONS

Csiba, M et al 'Liquid crystalline 5, 6–0–acetals of L–galactono–1,4–lactone prepared by a microwave irradiation on Montmorillonite' CA 118:223285, 1993.*
S. Morgenlie, "Synthesis of di–O–isopropylidene derivaties of L–fructose", *Carbohydrate Research*, No. 107, pp. 137–141, Amsterdam, NL, 1982.
D. Ono et al., "Biodegradation of Different Carboxylate Types of Cleavable Surfactants Bearing a 1,3–Dioxolane Ring", *J. of Amer. Oil Chemists Soc.*, 72(7):853–856, 1995.
K.A. Wilk et al., Synthesis and Hydrolysis of Chemodegradable Cationic Surfactants Containing the 1,3–Dioxolane Moiety, *J. of Amer. Oil. Chemists Soc.*, 71(1):81–85, 1994.
T. Kida et al., "New Cleavable Surfactants Derived from Glucono–1,5–Lactone", *J. of Amer. Oil Chemists Soc.*, 71(7):705–710, 1994.

\* cited by examiner

*Primary Examiner*—Amelia Owens
(74) *Attorney, Agent, or Firm*—Millen, White, Zelano & Branigan, P.C.

(57) ABSTRACT

The invention relates to cleavable surfactants of formula:

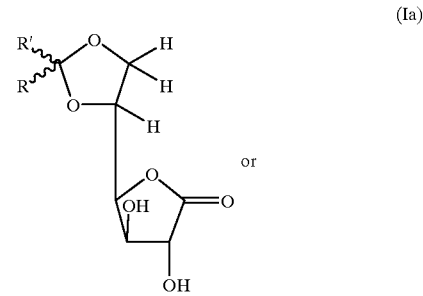

(Ia)

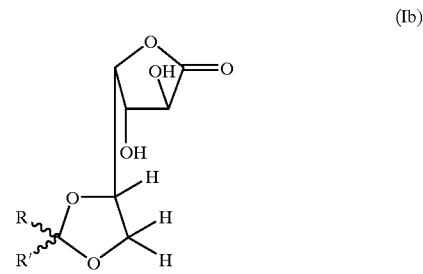

(Ib)

in which R' and R, which may be identical or different, represent a hydrogen atom or a linear or branched, saturated or unsaturated alkyl radical, the sum of the carbon atoms of R' and R being between 5 and 42.

The invention also relates to the corresponding derivatives obtained by alkaline hydrolysis or amidation.

The invention furthermore relates to the preparation of these surfactants from glucono-1(5)-lactone and a compound of formula R—CO—R' in the presence of an acid catalyst, R and R' having the meaning given above.

The surfactants are used in particular in emulsion polymerization and in the field of cosmetics.

23 Claims, No Drawings

5,6-O-ALKYLIDENE GLUCONO-1(4)-LACTONES AND DERIVATIVES, PROCESSES FOR THEIR PREPARATION AND USES THEREOF

FIELD OF THE INVENTION

The invention relates to 5,6-O-alkylidene glucono-1(4)-lactones and to the corresponding derivatives obtained by alkaline hydrolysis or amidation. The invention also relates to processes for the preparation of these compounds and to their uses.

BACKGROUND OF THE INVENTION

Surfactants are made use of in many organic chemistry syntheses.

This is the case, in particular, of emulsion polymerization processes, which offer the advantage of a high rate of reaction and a high degree of polymerization.

The emulsion polymerization, for example in water, generally uses a hydrophobic monomer, a surfactant forming micellar structures and an initiator. The reaction takes place inside the said structures and continues until the monomer is completely converted. Depending on the size of the polymer particles stabilized by the surfactant in the medium, a latex or a suspension is obtained.

Separation of the particles from the medium is made difficult by the presence of a surfactant, which tends to form highly stable emulsions or foams during the extraction step.

To overcome these drawbacks, cleavable surfactants have been proposed, inter alia, which are capable of decomposing into non-surfactant intermediates by an acid hydrolysis.

Among these surfactants, mention may be made of compounds having a labile structure of the 1,3-dioxane type, obtained by condensation of an aliphatic diol and a bromo aldehyde [WANG G. W. et al., JAOCS, Vol. 72, No. 1, pp. 83–87, 1995; JAOCS, Vol. 71, No. 7, pp. 727–730, 1994; JAOCS, Vol. 70, No. 7. pp. 731–732, 1993; J. Colloid and Interface Science, Vol. 173, pp. 49–54, 1995] or by acetalization of N-acetylglucosamine [KIDA T. et al., JAOCS, Vol. 72,-No. 7, pp. 773–780, 1995] or of glucono-1(5)-lactone [KIDA T. et al., JAOCS, Vol. 71, No. 7, pp. 705–710, 1994].

Mention may also be made of compounds having a labile structure of the 1,3-dioxolane type, such as cationic derivatives of alkyl 1,3-dioxolane (in the form of trimethylammonium bromides) [WILK K. A. et al., JAOCS, Vol. 71, No. 1, pp. 81–85, 1994], anionic derivatives containing one or two carboxylate groups [ONO D. et al., JAOCS, Vol. 72, No. 7, pp. 853–856, 1995] and nonionic derivatives obtained from L-galactono-1(4)-lactone.

The preparation of the surfactants which have just been mentioned usually requires many steps in which solvents and/or toxic reactants (for example dimethylformamide, benzene or acrolein) or starting materials that are not readily available (for example L-galactono-1(4)-lactone) are used.

It goes without saying that there is a great demand to have available novel cleavable surfactants which, in addition, are compatible with the skin and mucous membranes, are biodegradable and may be produced on an industrial scale from readily accessible starting materials.

SUMMARY OF THE INVENTION

The present invention thus relates, firstly, to surfactants which satisfy the abovementioned criteria. These surfactants are 5,6-O-alkylidene glucono-1(4)-lactones of formula:

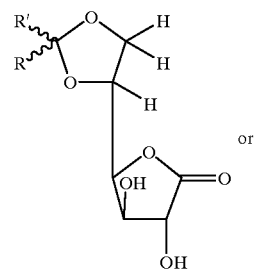

(Ia)

or

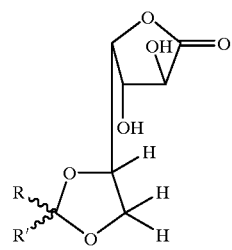

(Ib)

in which R' and R, which may be identical or different, represent a hydrogen atom or a linear or branched, saturated or unsaturated alkyl radical, the sum of the carbon atoms of R' and R being between 5 and 42, and preferably between 5 and 21.

The subject of the invention is also a process for the preparation of the abovementioned compounds of formula (I), which consists in reacting glucono-1(5)-lactone with a compound of formula R'—CO—R in the presence of an acid catalyst, R' and R having the meaning given above.

Another subject of the invention relates to the compounds obtained by alkaline hydrolysis of the abovementioned compounds of formula (I), these compounds corresponding to the formula:

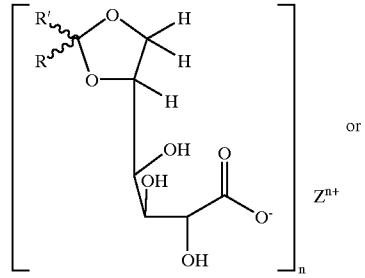

(IIa)

or

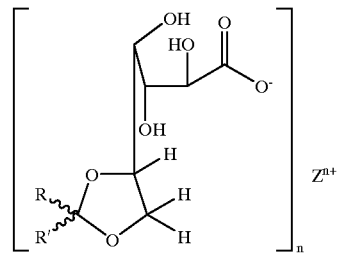

(IIb)

in which:

R' and R have the meaning given above, $Z^{n+}$ represents a cation of an alkali metal or alkaline-earth metal, or a quaternary ammonium of formula:

in which:

R$_2$, R$_3$, R$_4$ and R$_5$, which may be identical or different, represent an alkyl or hydroxyalkyl radical containing 1 to 18 carbon atoms, an alkylaryl radical containing 7 to 18 carbon atoms or a basic amino acid residue, and n is the valency of the cation.

Another subject of the invention relates to the compounds obtained by amidation of the abovementioned compounds of formula (I), these compounds corresponding to the formula:

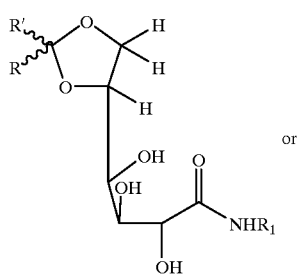

(IIIa)

or

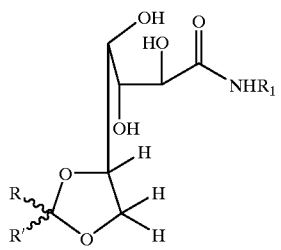

(IIIb)

in which:

R' and R have the meaning given above,

R$_1$ represents a linear or branched mono- or polyhydroxyalkyl radical containing 2 to 12 carbon atoms and preferably 2 to 6 carbon atoms.

Another subject of the invention relates to compositions, in particular detergent or cosmetic compositions, containing compounds of formula (I) and/or (II) and/or (III).

The invention is described in detail in the following text:

A. PREPARATION OF THE COMPOUNDS OF FORMULA (1)

The alkylidene lactones of formula (I) are obtained by reacting glucono-1(5)-lactone with a compound of formula R'—CO—R in which R' and R have the meaning given above, in the presence of an acid catalyst and in an anhydrous solvent.

The preferred glucono-1(5)-lactone is D-glucono-1(5)-lactone.

The compound of formula R'—CO—R is most particularly chosen from aldehydes such as n-heptanal, n-octanal, n-nonanal, n-decanal, n-undecanal, n-dodecanal, n-tetradecanal and 10-undecenal and ketones such as 2-heptanone, 2-octanone, 3-octanone, 2-nonanone, 3-nonanone, 2-decanone, 3-decanone, 2-undecanone and 6-undecanone.

The catalyst is generally chosen from hydrochloric acid, sulphuric acid, alkylsulphuric acids such as decyl- or laurylsulphuric acid, sulphonic acids such as benzenesulphonic, para-toluenesulphonic or camphorsulphonic acid, alkylsulphonic acids such as methanesulphonic, decylsulphonic, laurylsulphonic or sulphosuccinic acid or an alkyl sulphosuccinate, for example decyl or lauryl sulphosuccinate, perhalohydric acids such as perchloric acid or hypophosphorous acid, and mixtures of these acids.

Preferably, sulphuric acid, an alkylsulphuric acid, para-toluenesulphonic acid, methanesulphonic acid, sulphosuccinic acid or an alkyl sulphosuccinate, or hypophosphorous acid or a mixture of these acids is used.

The solvent is generally chosen from alkanes such as hexane or heptane, oxide ethers such as diethyl ether, isopropyl ether, dipropyl ether, dibutyl ether, diisobutyl ether, dioxane or diethylene glycol dimethyl ether, halogenated hydrocarbons such as dichloromethane, chloroform or dichloroethane, solvents of the amide type such as N-methylformamide, N,N-dimethylformamide, N,N-dimethylacetamide or N-methyl-2-pyrrolidone, sulphoxides such as dimethyl sulphoxide, nitrites such as acetonitrile, aromatic solvents such as toluene or xylene, and mixtures of these solvents.

Preferably, a mixture of two immiscible solvents is used, for example a mixture of an apolar solvent and a polar solvent, such as a hexane/N,N-dimethylformamide mixture.

The ratio by volume of the apolar solvent to the polar solvent is generally between 0.5 and 10 and preferably between 1 and 4.

In the process according to the invention, from 0.5 to 1.2 molar equivalents and preferably 0.7 to 1 equivalent of the compound of formula R'—CO—R and $0.5 \times 10^{-3}$ to 1 molar equivalent, and preferably $1 \times 10^{-2}$ to 0.5 equivalent, of acid catalyst are generally used per 1 molar equivalent of glucono-1(5)-lactone.

From 2 to 20 weight equivalents, and preferably 4 to 12 equivalents, of solvent are generally used per 1 weight equivalent of glucono-1(5)-lactone.

The reaction is generally carried out at the reflux temperature of the solvent, with trapping out of the water formed by means of a suitable system, for example of the Florentine flask type, at a temperature generally of between 25 and 200° C. and preferably 50 to 120° C.

The reaction time may range from 1 to 50 hours and preferably 5 to 40 hours.

The reaction is generally carried out at a pressure of between 0.013 and 101.325 kPa, and preferably at atmospheric pressure.

After the reaction, the catalyst present in the reaction medium is removed by filtration, for example through neutral alumina or a silica/neutral alumina mixture.

An oil, generally of yellow to orange-brown colour, containing the compounds of formula (I) is recovered.

These compounds may optionally be separated, for example by chromatography on a column of silica and/or precipitation and/or crystallization in a solvent chosen from those mentioned above, esters such as ethyl, propyl or butyl acetate, and alcohols such as methanol, ethanol, propanol or butanol.

B. PREPARATION OF THE COMPOUNDS OF FORMULA (II)

The compounds of formula (II) are prepared by reacting the compounds of formula (I) and a base of formula $Z^{n+}(OH^-)_n$ in the presence of a solvent, $Z^{n+}$ and n having the meaning given above.

By way of illustration of such a base, mention may be made of sodium hydroxide, potassium hydroxide and magnesium hydroxide.

It goes without saying that a precursor of such a base may also be used, for example a carbonate or a hydrogencarbonate of an alkali metal such as sodium or potassium, or a basic alumina.

The base is generally used in a proportion of from 0.8 to 1.6 molar equivalent, preferably 1 to 1.4 equivalent, per 1 molar equivalent of the compound of formula (I).

The solvent is generally chosen from alkanes, oxide ethers, amides and aromatics as defined above in step A), water, alcohols such as methanol, ethanol, propanol, isopropanol and butanol, as well as mixtures of these compounds.

Preferably, water, alcohols and alcohol/water mixtures, for example methanol/water and ethanol/water, are used.

The reaction is generally carried out at a temperature of between 0 and 150° C., preferably between 25 and 100° C., for a period which may range from 15 minutes to 48 hours, preferably from 30 minutes to 12 hours, and preferably at atmospheric pressure.

After removing the solvent, for example by evaporation under reduced pressure, and optionally recrystallizing in a solvent defined above, the compounds of formula (II) are recovered.

C. PREPARATION OF THE COMPOUNDS OF FORMULA (III)

The compounds of formula (III) are obtained by reacting alkylidene lactones of formula (I) and an amine of formula $R_1NH_2$ in which $R_1$ has the meaning given above, in the presence of an anhydrous solvent.

By way of illustration of the amines, mention may be made of 2-aminoethanol, 1-amino-2-propanol, 3-amino-1-propanol, 2-amino-2-(hydroxymethyl)-1,3-propanediol and 1-amino-1-deoxyglucitol. Preferably, 2-aminoethanol, 2-amino-2-(hydroxymethyl)-1,3-propanediol and 1-amino-1-deoxyglucitol are used.

The solvent is generally chosen from the solvents or mixtures of solvents mentioned above in step B, with the exception of water or mixtures containing water. Alcohols such as methanol or ethanol are preferred.

It has been observed that the presence of water is liable to affect the yield and/or kinetics of the reaction, in particular by hydrolysis of the lactone. For this reason, the process is advantageously performed in the presence of a dehydrating agent known to those skilled in the art, added in a proportion of from 0.01 to 10 weight equivalents, preferably 0.5 to 2 equivalents, per 1 weight equivalent of the compound of formula (I).

The reaction is generally carried out at a temperature of between 0 and 200° C., preferably 10 and 100° C., for a period of from 15 minutes to 72 hours, preferably 1 to 48 hours.

After the reaction, and, where appropriate, after elimination of the dehydrating agent, for example by filtration, the compounds of formula (III) are recovered.

These compounds may optionally be separated, for example by chromatography on a column of silica and recrystallization from a solvent chosen from those mentioned above in step A) or B).

The alkylidene lactones of formulae (I), (II) and (III) may be used in many fields which require surfactant properties in basic or neutral medium and a capacity for cleavage in acidic medium, for example in any type of emulsion reaction.

In addition to their surfactant properties (solubilizing, emulsifying, foaming and wetting), the compounds according to the invention have the advantage of not attacking the skin and mucous membranes. This character allows them to be used in compositions intended for hygiene, for example shampoos, and hair or cosmetic compositions, for example beauty milks, creams or ointments.

The foaming power and the capacity to soften the skin of the compounds of the invention may also be exploited in order to prepare compositions for the bath (foam baths) or the shower (shower gel), and soaps, in particular of the syndet (synthetic detergent) type.

The compounds according to the invention may also be used as antistatic agents for the treatment of textiles, wetting agents for the treatment of leathers and metals, and emulsifiers in the petroleum field.

The examples which follow illustrate the invention.

In these examples, the following methods of analysis are used:

The $R_f$ is measured by thin layer chromatography on silica (Kieselgel 60F$_{254}$; thickness of the film: 200 $\mu$m; particle size: 5–10 $\mu$m; Merck). The migration solvent is a 3/2 (v/v) ethyl acetate/hexane mixture containing traces of tetrabutylammonium hydroxide (Examples 1 to 8) or 5/1 (v/v) ethyl acetate/methanol mixture (Examples 13 to 16).

The migration spots are developed by spraying with sulphuric acid at 50% by volume in water and heating to 120° C. for 2 minutes.

Nuclear magnetic resonance (NMR)

The spectra are acquired using a Bruker AC 300 multinuclear machine at 300 MHz ($^1$H) and 75 MHz ($^{13}$C) in acetone-d$_6$ (Examples 1 to 8 and 13 to 20) or in D$_2$O at 80° C. (Examples 9 to 12). The internal reference is tetramethylsilane.

The chemical shifts are expressed in ppm and the coupling constants (J) in Hz.

Infrared (IR) spectrography

The spectra are acquired using a Perkin Elmer 1720X Fourier transform machine, on a film between two NaCl discs (for the liquid compounds) or KBr discs for the solid compounds (2%). The values are expressed in wave numbers per cm.

Meltina point (or decomposition temperature): measured on a Bachi machine, expressed in °C (uncorrected).

Foaming power: measured by bubbling nitrogen through at a constant flow rate (4 l/h) through a sinter (permeability to water: 980 ml/h at 40° C. and 1100 ml/h at 60° C.) placed at the base of a thermostatically-regulated graduated cylinder (320 mm×36.5 mm) containing 30 ml of an aqueous solution, under the following conditions:

Examples 4 to 6, 10 and 11
  Concentration: 1 g/l; pH=11.5; 40° C.
Examples 13 to 16
  Concentration: 0.2 g/l; pH=7; 60° C.
Examples 18 and 19
  Concentration: 1 g/l; pH=7; 40° C.

Wetting power: measured according to the standard NF T 73-406, which consists in monitoring, as a function of time, the change in the contact angle, expressed in degrees, of a drop of 3 $\mu$l of a solution (1 g/l; 25° C.) of the test compound placed on a raw cotton fabric.

Surface tension ($\gamma$CMC): measured by tensiometry according to the stirrup tear method (ISO standard 304) modified in that the dimensions of the plate are equal to 25 mm×5 mm×0.1 mm. The results are expressed in mN/m.

Critical micelle concentration (CMC) measured according to ISO standard 4311. The results are expressed in g/l.

The foaming power, the wetting power, the surface tension and the critical micelle concentration are evaluated in comparison with the following reference compounds:

alkylpolyglucosides: Oramix GG 110 ($C_8/C_{10}$; DP 1.5; active material: 60%) and Oramix NS 10 ($C_{10}/C_{12}/C_{14}$; DP 1.3; active material: 55%) marketed by Seppic.
  cocoamphoacetates: Miranol Ultra ($C_{32}$; active material: 32%; NaCl: 7%) marketed by Rhône-Poulenc.

oxyethylenated lauryl ether sulphates: Genapol LRO (2 EO; $C_{12}/C_{14}$; active material: 27%) and Genapol ZRO (3 OE; C12/C14; active material: 27.5%) marketed by Hoechst.

EXAMPLES 1 TO 8

42.8 g (0.24 mol) of D-glucono-1(5)-lactone (Ref. G200-1; Aldrich), 0.2 mol of a fatty aldehyde, 500 ml of anhydrous hexane, 300 ml of N,N-dimethylformamide (4Å molecular sieves) and 7.6 g (0.04 mol) of para-toluenesulphonic acid monohydrate are introduced into a three-necked round-bottomed flask over which is mounted a Florentine flask and a condenser fitted with a guard tube ($CaCl_2$).

The fatty aldehyde is identified as follows:

| | | |
|---|---|---|
| heptanal; | 22.84 g (Ref. H212-0; Aldrich) | Example 1 |
| octanal; | 25.64 g (Ref. O 560-8; Aldrich) | Example 2 |
| nonanal; | 28.45 g (Ref. N3 080-3; Aldrich) | Example 3 |
| decanal; | 31.25 g (Ref. 12577-6; Aldrich) | Example 4 |
| undecanal; | 34.06 g (Ref. U 220-2; Aldrich) | Example 5 |
| 10-undecenal; | 33.65 g (Ref. 13 227-6; Aldrich) | Example 6 |
| dodecanal; | 36.86 g (Ref. D 22 200-3; Aldrich) | Example 7 |
| tetradecanal; | 42.47 g (Ref. T1 000-6; Aldrich) | Example 8 |

The reaction medium is stirred (300 revolutions/min) and maintained at reflux for 25 hours. After cooling (about 25° C.), the two-phase medium obtained is filtered through a column filled with neutral alumina (ICN N32-63) and concentrated at 70° C. (under atmospheric pressure and then reduced pressure).

The oil obtained is chromatographed on a column of silica (200–300 mesh ASTM; eluent: 2/1 (v/v) ethyl acetate/hexane) and recrystallized from a 2/1 (v/v) mixture (Examples 1 to 3) or 3/1 (v/v) mixture (Examples 4 to 8) of diethyl ether/hexane.

The characteristics of the 5,6-O-alkylidene lactones (I) obtained are presented below:

| EXAMPLE | YIELD (%) | MELTING POINT (° C.) | $R_f$ | IR (cm$^{-1}$) |
|---|---|---|---|---|
| 1 | 54 | 80–82 | 0.31 | 3600-3200, 2950-2853, 1762, 1470-1422, 1240, 1220-1105, 1055, 960 |
| 2 | 55 | 88–90 | 0.32 | 3600-3200, 2950-2850, 1752, 1470-1420, 1240, 1220-1100, 1060, 960 |
| 3 | 59 | 98–100 | 0.32 | 3600-3200, 2950-2863, 1773, 1471-1421, 1363, 1240, 1220, 1108, 1050, 962 |
| 4 | 63 | 104–106 | 0.33 | 3600-3200, 2950-2852, 1770, 1470-1421, 1363, 1220, 1108, 1055, 960 |
| 5 | 65 | 109–111 | 0.34 | 3600-3200, 2950-2862, 1773, 1470-1421, 1363, 1220, 1106, 1062, 960 |
| 6 | 69 | 97–99 | 0.33 | 3200, 3083, 2982, 2851, 1763, 1469-1418, 1238, 1212, 1121, 1109, 1060, 964 |
| 7 | 68 | 105–107 | 0.36 | 3600-3200, 2950-2850, 1777, 1471-1418, 1363, 1245, 1220, 1100, 1065, 962 |
| 8 | 70 | 112–115 | 0.38 | 3600-3200, 2950-2850, 1768, 1471-1419, 1363, 1220, 1107, 1062, 962 |

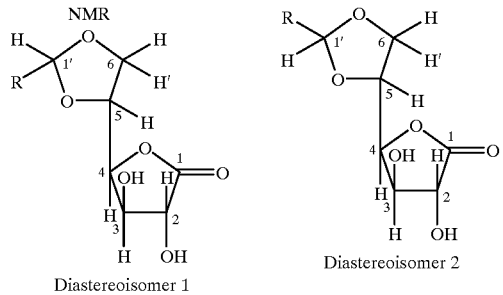

Diastereoisomer 1   Diastereoisomer 2

EXAMPLE 2

$^1$H NMR:

diastereoisomer 1: δ 5.39 (m, OH2), 4.92 (m, OH3), 4.86 (t, J=4.8, H1'), 4.74 (dd, J=5, H4), 4.46–4.38 (m, H5+H3), 4.17–4.12 (m, H2), 3.98 (dd, J=4.7 and 8.6, H6), 3.92 (dd, J=7 and 8.6, H6'), 1.67–1.52 (m, C$\underline{H}$2), 1.42–1.29 (m, (C$\underline{H}$2)$_{n-1}$), 0.88 (t, J=6.6, C$\underline{H}$3).

diastereoisomer 2: δ 5.39 ((m, OH2), 5.01 (t, J=4.8, H1'), 4.79 (m, OH3), 4.59 (dd, J=4.3 and 6.2, H4), 4.46–4.38 (m, H5), 4.36 (dt, J=2.4 and 5.7, H3), 4.17–4.12 (m, H2+H6), 3.86 (dd, J=7.3 and 8.6, H6'), 1.67–1.52 (m, C$\underline{H}$2), 1.42–1.29 (m, (C$\underline{H}$2)$_{n-1}$), 0.88 (t, J=6.6, C$\underline{H}$3).

$^{13}$C NMR

δ 175.35–175.32 (C1), 105.31–105.22 (C1'), 82.37–82.32 (C4), 75.06–74.82 (C2), 73.99–73.90 (C5), 73.79–73.61 (C3), 67.38–67.23 (C6), 35.04–34.61–32.50–30.24–29.96–24.69–24.66–23.28 (CH2)$_n$, 14.34 (C$\underline{H}$3).

EXAMPLE 3

H NMR:

diastereoisomer 1: δ 5.45 (d, J=4.8, OH2), 5.00 (d, J=5, OH3), 4.87 (t, J=4.8, H1'), 4.74 (dd, J=5, H4), 4.46–4.38 (m, H5+H3), 4.18–4.12 (m, H2), 3.98 (dd, J=4.7 and 8.6, H6), 3.92 (dd, J=7 and 8.6, H6'), 1.65–1.56 (m, C$\underline{H}$2), 1.41–1.29 (m, (C$\underline{H}$2)$_{n-1}$), 0.88 (t, J=6.6, C$\underline{H}$3).

diastereoisomer 2: δ 5.48 (d, J=4.6, OH2), 5.01 (t, J=4.8, H1'), 4.85 (d, J=4.7, OH3), 4.60 (dd, J=4.3 and 6.2, H4), 4.46–4.38 (m, H5), 4.35 (dt, J=2.4 and 5.7, H3), 4.18–4.13 (m, H2+H6), 3.86 (dd, J=7.3 and 8.6, H6'), 1.65–1.56 (m, C$\underline{H}$2), 1.41–1.29 (m, (C$\underline{H}$2)$_{n-1}$), 0.88 (t, J=6.6, C$\underline{H}$3).

$^{13}$C NMR:

δ 175.25–175.26 (C1), 105.30–105.20 (C1'), 82.33–82.27 (C4), 75.06–74.82 (C2), 73.95–73.91 (C5), 73.76–73.63 (C3), 67.38–67.23 (C6), 34.69–34.59–32.56–30.24–29.94–24.68–24.64–23.28 (CH2)$_n$, 14.33 (C$\underline{H}$3).

EXAMPLE 7

$^1$H NMR:

diastereoisomer 1: δ 5.44 (d, J=4.8, OH2), 4.99 (d, J=5, OH3), 4.86 (t, J=4.8, H1'), 4.75 (dd, J=5, H4), 4.46–4.39 (m, H5+H3), 4.19–4.13 (m, H2), 3.98 (dd, J=4.7 and 8.6, H6), 3.92 (dd, J=7 and 8.6, H6'), 1.67–1.56 (m, C$\underline{H}$2), 1.39–1.29 (m,(C$\underline{H}$2)$_{n-1}$), 0.88 (t, J=6.6, C$\underline{H}$3).

diastereoisomer 2: δ 5.47 (d, J=4.6, OH2), 5.01 (t, J=4.8, H1'), 4.86 (d, J=4.7, OH3), 4.60 (dd, J=4.3 and 6.2, H4), 4.46–4.39 (m, H5), 4.35 (dt, J=2.4 and 5.7, H3), 4.19–4.13 (m, H2+H6), 3.86 (dd, J=7.3 and 8.6, H6'), 1.67–1.56 (m, C$\underline{H}$2), 1.39–1.29 (m, (C$\underline{H}$2)$_{n-1}$), 0.88 (t, J=6.6, C$\underline{H}$3)

$^{13}$C NMR:

δ 175.29–175.29 (C1), 105.31–105.22 (C1'), 82.33–82.28 (C4), 75.05–74.82 (C2), 73.97–73.91 (C5), 73.78–73.63 (C3), 67.37–67.23 (C6), 34.71–34.61–32.50–30.36–30.33–30.28–24.67–24.66–23.30 (C$\underline{H}$2)$_n$, 14.36 (C$\underline{H}$3).

EXAMPLE 8

$^1$H NMR:

diastereoisomer 1: δ 5.33 (d, J=4.8, OH2), 4.89 (d, J=5, OH3), 4.86 (t, J=4.8, H1'), 4.73 (dd, J=5, H4), 4.46–4.39 (m, H5+H3), 4.19–4.12 (m, H2), 3.98 (dd, J=4.7 and 8.6, H6), 3.92 (dd, J=7 and 8.6, H6'), 1.68–1.56 (m, C$\underline{H}$2), 1.45–1.29 (m, (C$\underline{H}$2)$_{n-1}$), 0.88 (t, J=6.6, C$\underline{H}$3).

diastereoisomer 2: δ 5.36 (d, J=4.6, OH2), 5.02 (t, J=4.8, H1'), 4.77 (d, J=4.7, OH3), 4.59 (dd, J=4.3 and 6.2, H4), 4.46–4.38 (m, H5), 4.35 (dt, J=2.4 and 5.7, H3), 4.18–4.12 (m, H2+H6), 3.86 (dd, J=7.3 and 8.6, H6'), 1.68–1.56 (m, C$\underline{H}$2), 1.45–1.29 (m, (C$\underline{H}$2)$_{n-1}$), 0.88 (t, J=6.6, C$\underline{H}$3).

$^{13}$C NMR:

δ 175.27–175.27 (C1), 105.37–105.27 (C1'), 82.35–82.31 (C4), 75.10–74.88 (C2), 74.02–73.85 (C5), 73.70–73.61 (C3), 67.4–67.2 (C6), 34.75–34.65–32.62–30.39–30.37–30.36–30.24–29.96–24.69–24.68–23.31 (C$\underline{H}$2)$_n$, 14.3 (C$\underline{H}$3).

EXAMPLES 9 TO 12

10 mmol of 5,6-O-alkylidenegluconolactone (diastereoisomers 1 and 2) according to Example 2, 3, 7 or 8 (2.88 g, 3.02 g, 3.44 g and 3.72 g respectively), 12 mmol of sodium hydroxide (0.48 g), 50 ml of methanol and 1 ml of water are introduced into a 100 ml one-necked round-bottomed flask and the mixture is heated at reflux for 3 hours. The product obtained after evaporation of the solvent (40° C.; 2.4 kPa) is recrystallized from a 27/3 (v/v) ethanol/water mixture.

The precipitate obtained is filtered off (sinter funnel), washed with absolute ethanol and dried (25° C.; 2.4 kPa).

The characteristics of the 5,6-O-alkylidenegluconates (II) obtained (Examples 9 to 12 respectively) are presented below.

| EXAMPLE | YIELD (%) | MELTING POINT (° C.) | IR (cm$^{-1}$) |
|---|---|---|---|
| 9 | 50 | 213–215 | 3490-3220, 2930, 2855, 1635, 1460, 1377, 1260, 1118, 1056, 960 |
| 10 | 50 | 214–216 | 3490-3220, 2924, 2856, 1633, 1460, 1380, 1269, 1119, 1054, 964 |
| 11 | 62 | 215–217 | 3498-3220, 2930, 2855, 1595, 1471, 1344, 1265, 1150, 1057, 953 |
| 12 | 73 | 220–222 | 3492-3220, 2921, 2849, 1599, 1470, 1377, 1266, 1150, 1056, 953 |

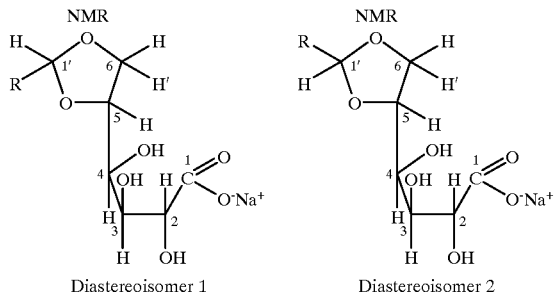

Diastereoisomer 1    Diastereoisomer 2

EXAMPLE 9

$^1$H NMR:

diastereoisomer 1: δ 4.90 (t, J=5, H1'), 4.26–4.17 (m, H4), 4.12 (d, J=3, H2), 4.05–3.80 (m, H6'+H6), 3.93–3.86 (m, H5+H3), 1.73–1.61 (m, C$\underline{H}$2), 1.44–1.32 (m, (C$\underline{H}$2)$_{n-1}$), 0.89 (t, J=6.6, C$\underline{H}$3).

diastereoisomer 2: δ 5.08 (t, J=5, H1'), 4.26–4.17 (m, H6+H4), 4.12 (d, J=3, H2), 3.93–3.86 (m, H5+H6'+H3), 1.73–1.61 (m, C$\underline{H}$2), 1.44–1.32 (m, (C$\underline{H}$2)$_{n-1}$), 0.89 (t, J=6.6, C$\underline{H}$3).

$^{13}$C NMR:

δ 179.28–179.28 (C1), 105.97–105.88 (C1'), 77.02–76.57 (C4), 74.60–73.41 (C2), 73.21–72.98 (C5), 72.81–72.28 (C3), 67.56–67.12 (C6), 34.62–34.30–32.47–32.42–30.17–30.05–29.79–24.92–24.63–23.24 (C$\underline{H}$2)$_n$, 14.54 (C$\underline{H}$3).

EXAMPLE 10

$^1$H NMR:

diastereoisomer 1: δ 4.88 (t, J=5, H1'), 4.21–4.14 (m, H4), 4.11 (d, J=3, H2), 4.04–3.79 (m, H6'+H6), 3.93–3.91 (m, H5+H3), 1.65–1.54 (m, C$\underline{H}$2), 1.45–1.32 (m, (C$\underline{H}$2)$_{n-1}$), 0.89 (t, J=6.6, C$\underline{H}$3)

diastereoisomer 2: δ 5.07 (t, J=5, H1'), 4.14–4.21 (m, H6+H4), 4.11 (d, J=3, H2), 3.93–3.91 (m, H5+H6'+H3), 1.65–1.54 (m, C$\underline{H}$2), 1.45–1.32 (m, (C$\underline{H}$2)$_{n-1}$), 0.89 (t, J=6.6, C$\underline{H}$3).

$^{13}$C NMR:

δ 179.30–179.28 (C1), 105.91–105.91 (C1'), 77.91–76.55 (C4), 74.95–73.50 (C2), 73.70–72.58 (C5), 72.73–72.21 (C3), 67.87–67.49 (C6), 34.81–34.52–32.65–32.42–30.43–30.31–29.98–25.05–24.75–23.44 (C$\underline{H}$2)$_n$, 14.54 (C$\underline{H}$3).

EXAMPLE 11

$^1$H NMR:

diastereoisomer 1: δ 4.89 (t, J=5, H1'), 4.22–4.14 (m, H4), 4.10 (d, J=3, H2), 4.03–3.82 (m, H6'+H6), 3.95–3.92 (m, H5+H3), 1.96–1.59 (m, C$\underline{H}$2), 1.45–1.32 (m, (C$\underline{H}$2)$_{n-1}$), 0.88 (t, J=6.6, C$\underline{H}$3).

diastereoisomer 2: δ 5.06 (t, J=5, H1'), 4.22–4.14 (m, H6+H4), 4.10 (d, J=3, H2), 3.95–3.92 (m, H5+H6'+H3), 1.96–1.59 (m, C$\underline{H}$2), 1.45–1.32 (m, (C$\underline{H}$2)$_{n-1}$), 0.88 (t, J=6.6, C$\underline{H}$3).

13C NMR:

δ 179.30–179.30 (C1), 105.98–105.83 (C1'), 77.07–76.62 (C4), 74.64–73.46 (C2), 73.27–72.90 (C5), 72.79–72.33 (C3), 67.51–67.05 (C6), 34.86–34.48–32.76–32.42–30.59–30.52–30.36–29.79–25.22–24.83–23.41–22.39 (CH2)$_n$, 14.62 (CH3)

EXAMPLE 12

1H NMR:

diastereoisoimer 1: δ 4.89 (t, J=5, H1'), 4.22–4.16 (m, H4), 4.12 (d, J=3, H2), 4.05–3.80 (m, H6'+H6), 3.96–3.93 (m, H5+H3), 1.68–1.66 (m, CH2), 1.46–1.33 (m, (CH2)$_{n-1}$), 0.89 (t, J=6.6, CH3).

diastereoisomer 2: δ 5.07 (t, J=5, H1'), 4.22–4.16 (m, H6+H4), 4.12 (d, J=3, H2), 3.96–3.93 (m, H5+H6'+H3), 1.68–1.66 (m, CH2), 1.46–1.33 (m, (CH2)$_{n-1}$), 0.89 (t, J=6.6, CH3).

13C NMR

δ 179.37–179.37 (C1), 105.05–105.89 (C1'), 77.12–76.71 (C4), 74.73–73.56 (C2), 73.36–72.94 (C5), 72.83–72.30 (C3), 67.58–67.13 (C6), 35.03–34.63–34.30–32.86–32.42–30.79–30.70–30.52–24.92–24.97–23.49 (CH2)$_n$, 14.65 (CH3).

The characteristics of these compounds (Examples 13 to 16 respectively) are presented below.

| EXAMPLE | YIELD (%) | MELTING POINT (°C.) | R$_f$ | IR (cm$^{-1}$) |
|---|---|---|---|---|
| 13 | 53 | 150–152 | 0.42 | 3600–3200, 2922, 2855, 1650, 1555, 1123, 1024 |
| 14 | 64 | 154–156 | 0.43 | 3600–3200, 2921, 2871, 1659, 1551, 1133, 1028 |
| 15 | 70 | 150–152 | 0.44 | 3600–3200, 2924, 2853, 1655, 1552, 1128, 1046 |
| 16 | 66 | 166–168 | 0.46 | 3600–3200, 2953, 2851, 1650, 1553, 1129, 1024 |

| | Foaming power | | | | | | |
|---|---|---|---|---|---|---|---|
| Time (s) | Ex. 13 | Ex. 14 | Ex. 15 | Ex. 16 | Miranol Ultra (comparative) | Oramix NS 10* (comparative) | Genapol ZRO (comparative) |
| 0 | 0 | 0 | 0 | 0 | 0 | 0 | 0 |
| 50 | 10 | 18 | 11 | 18 | 9 | 12 | 9 |
| 100 | 20 | 35 | 22 | 36 | 16 | 26 | 17 |
| 150 | 34 | 53 | 33 | 54 | 23 | 38 | 26 |
| 200 | 49 | 68 | 44 | 74 | 29 | 50 | 34 |

| | Foaming power | | | | | | | | | |
|---|---|---|---|---|---|---|---|---|---|---|
| Time (s) | Ex. 4 | Ex. 5 | Ex. 6* | Ex. 10 | Ex. 11 | Oramix CG 110* (comparative) | Oramix NS 10* (comparative) | Miranol Ultra (comparative) | Genapol LRO (comparative) | Genapol ZRO (comparative) |
| 0 | 0 | 0 | 0 | 0 | 0 | 0 | 0 | 0 | 0 | 0 |
| 50 | 10 | 14 | 20 | 10 | 14 | 11 | 12 | 10 | 12 | 10 |
| 100 | 19 | 26 | 36 | 23 | 29 | 24 | 26 | 22 | 24 | 22 |
| 150 | 30 | 40 | 50 | 35 | 43 | 38 | 38 | 36 | 36 | 36 |
| 200 | 40 | 56 | 65 | 44 | 58 | 51 | 50 | 48 | 48 | 50 |
| 250 | 50 | 69 | 79 | 57** | 71 | 64 | 63 | 62 | 61 | 64 |
| 300 | 60 | 83 | 92 | | 84 | 76 | 76 | 78 | 73 | 78 |
| 400 | 80** | 111 | 120 | | 111 | 101 | 101 | 100 | 100 | 104 |
| 500 | | 138 | 142 | | 134 | 124 | 123 | 126 | 125 | 132 |
| 600 bubbling stopped | | 165 | 163 | | 154 | 149 | 147 | 150 | 150 | 158 |
| 900 | | 145 | 158 | | 60 | 145 | 143 | 146 | 148 | 120 |
| 1200 | | 135 | 150 | | 0 | 140 | 136 | 140 | 140 | 118 |

*very fine foam
**foam broken by continuing the bubbling

EXAMPLES 13 TO 16

10 mmol of 5,6-O-alkylidenegluconolactone (diastereoisomers 1 and 2) according to Example 3, 4, 6 or 7 (3.02 g, 3.16 g, 3.28 g and 3.44 g respectively), 20 mmol (2.42 g) of 2-amino-2-(hydroxymethyl)-1,3-propanediol (Ref. 15,456-3; Aldrich), 50 ml of anhydrous methanol and 2 g of 3Å molecular sieves are introduced into a 100 ml three-necked round-bottomed flask and the mixture is stirred for 25 hours at 25° C.

After removal of the sieves (filtration through a sinter funnel), the filtrate obtained is concentrated (40° C.; 2.4 kPa) and the residue is chromatographed through a column filled with silica (35–70 μm; eluent: 5/1 (v/v) ethyl acetate/methanol). The eluate is concentrated (40° C.; 2.4 kPa) and the alkylidene gluconamide (III; R1=—C(CH$_2$OH)$_3$) is recovered in crystalline form.

-continued

| | | | | | | | |
|---|---|---|---|---|---|---|---|
| 250 | 65 | 85 | 57 | 89 | 35 | 63 | 41 |
| 300 | 81 | 103 | 69 | 106 | 41 | 76 | 50 |
| 400 | 112 | 135 | 100 | 142 | 52 | 101 | 64 |
| 500 | 140 | 152 | 134 | 192* | 63 | 123 | 76 |
| 600 bubbling stopped | 160 | 166 | 164 | | 74 | 147 | 85 |
| 900 | 80 | 50 | 136 | | 74 | 143 | 56 |
| 1200 | 40 | 25 | 73 | | 72 | 136 | 38 |

*foam broken by continuing the bubbling

| | Wetting power | | |
|---|---|---|---|
| TIME (s) | Example 13 | GENAPOL ZRO (comparative) | MIRANOL ULTRA (comparative) |
| 20 | 92.5 | 104.2 | 102.1 |
| 40 | 88.3 | 103.6 | 101.6 |
| 60 | 82.7 | 103.3 | 101.6 |
| 80 | 79.7 | 102.4 | 100.6 |
| 100 | 78.0 | 101.9 | 100.0 |

-continued

| 120 | 75.2 | 101.7 | 100.0 |
| 140 | 74.2 | 96.3 | 99.9 |
| 160 | 73.5 | 90.7 | 97.9 |
| 180 | 71.9 | 87.8 | 94.8 |
| 200 | 71.0 | 84.0 | 84.3 |
| θ200-θ20 | 21.5 | 20.2 | 17.8 |

| | CMC and γ CMC | | |
|---|---|---|---|
| | Example 13 | Example 15 | GENAPOL ZRO (comparative) |
| CMC (g/l) | 0.08 | 0.07 | 0.35 |
| γ CMC (mN/m) | 39.2 | 34.8 | 48 |

EXAMPLES 17 TO 20

6 mmol of 5,6-O-alkylidene gluconolactone (diastereoisomers 1 and 2) according to Example 2, 3, 7 or 8 (1.73 g, 1.81 g, 2.06 g and 2.23 g respectively), 9 mmol (0.55 g) of ethanolamine, 40 ml of anhydrous methanol and 1 g of 3Å molecular sieves are introduced into a 100 ml three-necked round-bottomed flask and the mixture is stirred for 3 hours at 25° C.

After removal of the sieves (filtration through a sinter funnel), the filtrate obtained is concentrated (40° C.; 2.4 kPa) and the residue is chromatographed on a column filled with silica (35–70 μm; eluent: 15/2 (v/v) ethyl acetate/methanol). The eluate is concentrated (40° C.; 2.4 kPa) and the alkylidene gluconamide (III; $R_1$=—$CH_2CH_2OH$) is recovered in crystalline form.

The characteristics of these compounds (Examples 17 to 20 respectively) are presented below:

| EXAMPLE | YIELD (%) | MELTING POINT (° C.) | IR (cm$^{-1}$) |
|---|---|---|---|
| 17 | 51 | 101–104 | 3521-3331, 2926, 2874, 1650-1620, 1450-1417, 1143, 1053, 957 |
| 18 | 52 | 100–102 | 3521-3211, 2941, 2871, 1636-1561, 1469-1417, 1145, 1055, 945 |
| 19 | 64 | 163–165 | 3521-3309, 2920, 2851, 1651-1552, 1469-1417, 1145, 1055, 954 |
| 20 | 63 | 167–169 | 3509-3318, 2930, 2849, 1651-1620, 1449-1417, 1145, 1055, 953 |

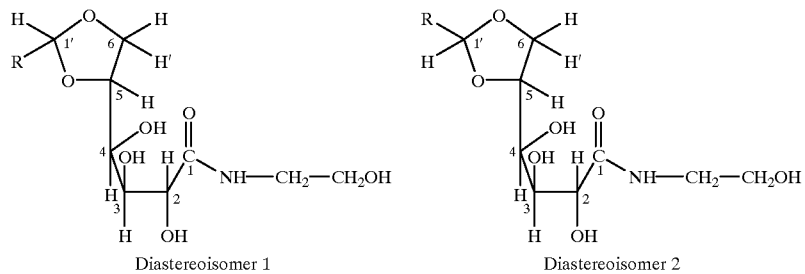

Diastereoisomer 1   Diastereoisomer 2

EXAMPLE 17

$^1$H NMR:

diastereoisomer 1: δ 7.56 (m, NH), 4.83 (m, H1'), 4.25 (t, J=4.6, H4), 4.13–4.09 (m, H2), 4.03–3.98 (m, H6'+H6), 3.89–3.85 (m, H3), 3.74 (m, H5) 3.63 (t, J=5.3, CH2—O), 3.37 (m, CH2—N), 2.94 (m, OH), 1.59–1.56 (m, CH2), 1.53–1.29 (m, (CH2)$_{n-1}$), 0.89 (t, J=6.4, CH3).

diastereoisomer 2: δ 7.65 (m, NH), 4.94 (m, H1'), 4.13–4.09 (m, H4+H6+H2), 3.89–3.85 (m, H6'+H5+H3), 3.63 (t J=5.3, CH2—O), 3.37 (m, (CH2—N), 2.94 (m, OH), 1.59–1.56 (m, CH2), 1.53–1.29 (m, (CH2)$_{n-1}$), 0.89 (t, J=6.4, CH3).

$^{13}$C NMR:

δ 173.76–173.76 (C1), 105.45–105.10 (C1'), 76.40–76.17 (C4), 74.95–73.95 (C2), 73.53–73.21 (C5), 72.39–71.92 (C3), 68.60–68.10 (C6), 61.62 (CH2—O), 42.46 (CH2—N), 34.96–34.89–32.55–30.61–30.29–30.01–24.83–24.76–23.32 (CH2)$_n$, 14.37 (CH3).

EXAMPLE 18

$^1$H NMR:

diastereoisomer 1: δ 7.58 (m, NH), 4.81 (m, H1'), 4.25 (t, J=4.6, H4), 4.13–4.10 (m, H2), 4.03–3.98 (m, H6'+H6), 3.89–3.84 (m, H3), 3.75 (m, H5) 3.63 (t, J=5.3, C$\underline{H}$2—O), 3.38 (m, C$\underline{H}$2—N), 3.02 (m, OH), 1.58–1.55 (m, C$\underline{H}$2), 1.53–1.29 (m, CH2)$_{n-1}$), 0.89 (t, J=6.4, C$\underline{H}$3).

diastereoisomer 2: δ 7.77 (m, N$\underline{H}$), 4.94 (m, H1'), 4.13–4.10 (m, H4+H6+H2), 3.89–3.84 (m, H6'+H5+H3), 3.63 (t, J=5.3, C$\underline{H}$2—O), 3.38 (m, C$\underline{H}$2—N), 3.02 (m, O$\underline{H}$), 1.58–1.55 (m, C$\underline{H}$2), 1.53–1.29 (m, (C$\underline{H}$2)$_{n-1}$), 0.88 (t, J=6.4, C$\underline{H}$3)

$^{13}$C NMR:

δ 173.85–173.85 (C1), 105.45–105.10 (C1'), 76.40–76.15 (C4), 74.78–73.89 (C2), 73.48–73.10 (C5), 72.40–71.93 (C3), 68.57–68.07 (C6), 61.58 ($\underline{C}$H2—O), 42.46 ($\underline{C}$H2-N), 35.77–34.95–34.88–32.61–30.39–30.33–30.29–30.10–24.83–24.75–23.32 ($\underline{C}$H2)$_n$, 14.37 ($\underline{C}$H3).

EXAMPLE 19

$^{1}$H NMR:

diastereoisomer 1: δ 7.55 (m, N$\underline{H}$), 4.83 (m, H1'), 4.25 (t, J=4.6, H4), 4.13–4.07 (m, H2), 4.02–3.98 (m, H6'+H6), 3.89–3.83 (m, H3), 3.75 (m, H5) 3.62 (t, J=5.3, C$\underline{H}$2—O), 3.37 (m, C$\underline{H}$2—N), 2.90 (m, OH), 1.60–1.56 (m, C$\underline{H}$2), 1.54–1.29 (m, CH2)$_{n-1}$), 0.88 (t, J=6.4, C$\underline{H}$3).

diastereoisomer 2: δ 7.70 (m, N$\underline{H}$), 4.94 (m, H1'), 4.13–4.07 (m, H4+H6+H2), 3.89–3.83 (m, H'6+H5+H3), 3.62 (t, J=5.3, C$\underline{H}$2—O), 3.37 (m, C$\underline{H}$2—N), 2.90 (m, O$\underline{H}$), 1.60–1.56 (m, C$\underline{H}$2), 1.54–1.29 (m, (C$\underline{H}$2)$_{n-1}$), 0.88 (t, J=6.4, C$\underline{H}$3).

$^{13}$C NMR:

δ 173.82–173.82 (C1), 105.45–105.11 (C1'), 76.42–76.17 (C4), 74.84–73.44 (C2), 73.21–73.15 (C5), 72.40–71.94 (C3), 68.56–68.06 (C6), 61.58 ($\underline{C}$H2—O), 42.47 ($\underline{C}$H2—N), 35.77–35.75–34.97–34.88–32.63–30.61–30.39–30.33–30.29–30.07–24.82–24.74–23.31 ($\underline{C}$H2)$_n$, 14.36 ($\underline{C}$H3).

EXAMPLE 20

$^{1}$H NMR:

diastereoisomer 1: δ 7.56 (m, N$\underline{H}$), 4.83 (m, H1'), 4.25 (t, J=4.6, H4), 4.13–4.08 (m, H2), 4.02–3.96 (m, H6'+H6), 3.89–3.84 (m, H3), 3.75 (m, H5), 3.62 (t, J=5.3, C$\underline{H}$2—O), 3.36 (m, C$\underline{H}$2—N), 2.96 (m, O$\underline{H}$), 1.60–1.56 (m, C$\underline{H}$2), 1.54–1.29 (m, CH2)$_{n-1}$), 0.89 (t, J=6.4, C$\underline{H}$3).

diastereoisomer 2: δ 7.70 (m, N$\underline{H}$), 4.93 (m, H1'), 4.13–4.08 (m, H4+H6+H2), 3.89–3.84 (m, H6'+H5+H3), 3.62 (t J=5.3, C$\underline{H}$2—O), 3.36 (m, C$\underline{H}$2—N), 2.96 (m, O$\underline{H}$), 1.60–1.56 (m, C$\underline{H}$2), 1.54–1.29 (m, (C$\underline{H}$2)$_{n-1}$), 0.89 (t, J=6.4, C$\underline{H}$3).

$^{13}$C NMR:

δ 173.71–173.64 (C1), 105.42–105.08 (C1'), 76.41–76.17 (C4), 74.76–73.91 (C2), 73.51–73.20 (C5), 72.35–71.87 (C3), 68.55–68.04 (C6), 61.71 ($\underline{C}$H2—O), 42.43 ($\underline{C}$H2—N), 35.75–35.70–34.95–34.87–32.63–32.58–30.61–30.40–30.29–30.36–30.34–30.26–30.07–24.83–24.75–23.32 ($\underline{C}$H2)$_n$, 14.37 ($\underline{C}$H3).

| | | Foaming power | | | |
|---|---|---|---|---|---|
| Time (s) | Example 18 | Example 19 | Oramix CG 110 (comparative) | Miranol Ultra (comparative) | Genapol ZRO (comparative) |
| 0 | 0 | 0 | 0 | 0 | 0 |
| 50 | 13 | 12 | 11 | 10 | 10 |
| 100 | 23 | 24 | 24 | 22 | 22 |

-continued

| | | Foaming power | | | |
|---|---|---|---|---|---|
| Time (s) | Example 18 | Example 19 | Oramix CG 110 (comparative) | Miranol Ultra (comparative) | Genapol ZRO (comparative) |
| 150 | 34 | 34 | 38 | 36 | 36 |
| 200 | 47 | 43 | 51 | 48 | 50 |
| 250 | 59 | 53 | 64 | 62 | 64 |
| 300 | 73 | 74 | 76 | 78 | 78 |
| 400 | 102 | 104 | 101 | 100 | 104 |
| 500 | 128 | 130 | 124 | 126 | 132 |
| 600 bubbling stopped | 154 | 160 | 149 | 150 | 158 |
| 900 | 149 | 152 | 145 | 146 | 120 |
| 1200 | 142 | 146 | 140 | 140 | 118 |

The preceding examples can be repeated with similar success by substituting the generically or specifically described reactants and/or operating conditions of this invention for those used in the preceding examples.

The entire disclosure of all applications, patents and publications, cited above, and of corresponding French application 97/04471, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. Compounds of formula:

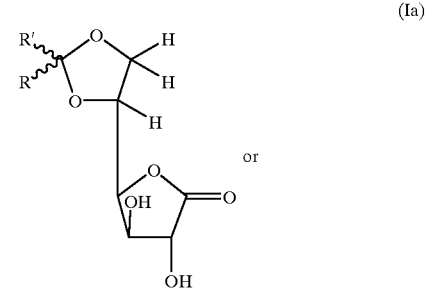

(Ia)

or

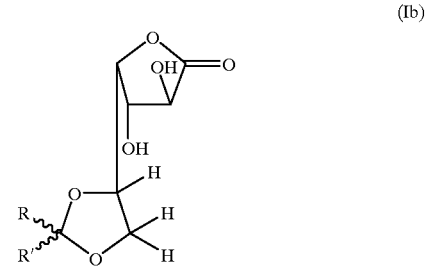

(Ib)

in which R' and R, which may be identical or different, represent a hydrogen atom or a linear or branched, saturated or unsaturated alkyl radical, the sum of the carbon atoms of R' and R being between 5 and 42.

2. Compounds according to claim 1, characterized in that the sum of the carbon atoms of R' and R is between 5 and 21.

3. A process for the preparation of compounds of formula:

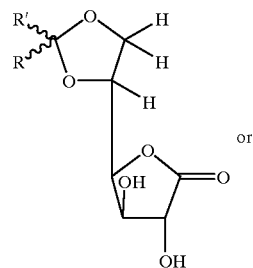
(Ia)

or

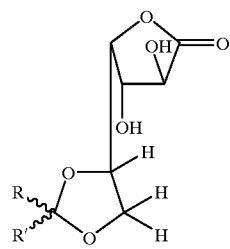
(Ib)

in which R' and R, which may be identical or different, represent a hydrogen atom or a linear or branched, saturated or unsaturated alkyl radical, the sum of the carbon atoms of R' and R being between 5 and 42, comprising reacting a glucono-1(5)-lactone with a compound of formula R'—CO—R, in the presence of an acid catalyst and in an anhydrous solvent.

4. A process according to claim 3, wherein the glucono-1(5) lactone is D-glucono-1(5)-lactone.

5. A process according to claim 3, in which the compound of formula R'—CO—R is n-heptanal, n-octanal, n-nonanal, n-decanal, n-undecanal, n-dodecanal, n-tetradecanal, 10-undecenal, 2-heptanone, 2-octanone, 3-octanone, 2-nonanone, 3-nonanone, 2-decanone, 3-decanone, 2-undecanone or 6-undecanone.

6. A process according to claim 3, in which from 0.5 to 1.2 molar equivalents of R'—CO—R and $0.5 \times 10^{-3}$ to 1 molar equivalent of acid catalyst are used per 1 molar equivalent of glucono-1(5)-lactone.

7. A process according to claim 3, in which 2 to 20 weight equivalents of solvent are used per 1 weight equivalent of glucono-1(5)-lactone.

8. A process according to claim 3, in which the solvent is chosen from alkanes, oxide ethers, halogenated hydrocarbons, amides, sulphoxides, nitriles and aromatics, and mixtures thereof.

9. Compounds of formula:

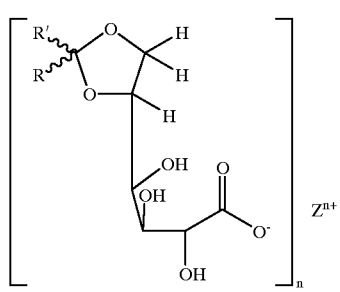
(IIa)

or

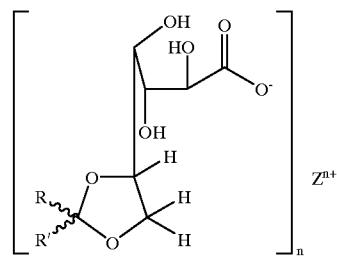
(IIb)

in which:

R' and R, which may be identical or different, represent a hydrogen atom or a linear or branched, saturated or unsaturated alkyl radical, the sum of the carbon atoms of R' and R being between 5 and 42.

$Z^{n+}$ represents a cation of an alkali metal or alkaline-earth metal, or a quaternary ammonium of formula:

in which $R_2$, $R_3$, $R_4$ and $R_5$, which may be identical or different, represent an alkyl or hydroxyalkyl radical containing 1 to 18 carbon atoms, an alkylaryl radical containing 7 to 18 carbon atoms or a basic amino acid residue, and n is the valency of the cation.

10. Compounds according to claim 9, characterized in that the sum of the carbon atoms of R' and R is between 5 and 21.

11. A process for the preparation of the compounds according to claim 9 comprising reacting a corresponding 5,6-O-alkylidine glucono-1(4)-lactone with a base of formula $Z^{n+}(OH^-)_n$ in the presence of a solvent.

12. A process according to claim 11, in which the base is chosen from sodium hydroxide, potassium hydroxide and magnesium hydroxide.

13. A process according to either of claim 11, in which 0.8 to 1.6 molar equivalents of base are used per 1 molar equivalent of the lactone.

14. Compounds of formula:

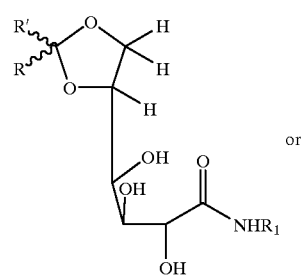
(IIIa)

or

-continued

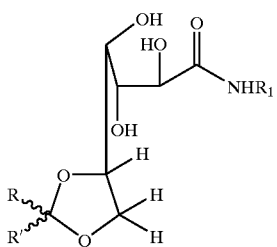

(IIIb)

in which:
R' and R, which may be identical or different, represent a hydrogen atom or a linear or branched, saturated or unsaturated alkyl radical, the sum of the carbon atoms of R' and R being between 5 and 42,
$R_1$ represents a linear or branched mono- or polyhydroxy-alkyl radical containing 2 to 12 carbon atoms.

15. Compounds according to claim 14, characterized in that the sum of the carbon atoms of R' and R is between 5 and 21.

16. A process for the preparation of the compounds according to claim 14 comprising reacting a corresponding 5,6-O-alkylidine glucono-1(4)-lactone with an amine of formula $R_1NH_2$ in the presence of an anhydrous solvent.

17. A process according to claim 16, in which the amine is 2-aminoethanol, 2-amino-2-(hydroxymethyl)-1,3-propanediol or 1-amino-1-deoxyglucitol.

18. Compounds of claim 1 of the formula (Ia).

19. Compounds of claim 1 of the formula (IIa).

20. An emulsion polymerization process comprising forming an emulsion of water and a monomer with an emulsifying agent which is a compound according to claim 1, and subjecting the resultant emulsion to polymerization conditions so as to polymerize the monomer.

21. A cosmetic composition comprising at least one compound according to claim 9.

22. A cosmetic composition comprising at least one compound according to claim 14.

23. A cosmetic composition comprising at least one compound of the formula:

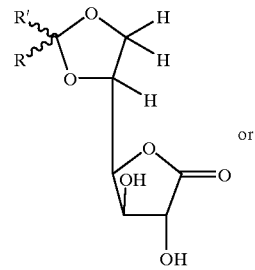

(Ia)

or

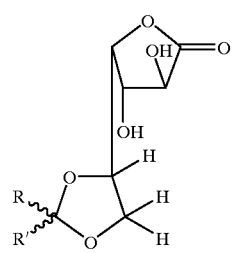

(Ib)

in which R' and R, which may be identical or different, represent a hydrogen atom or a linear or branched, saturated or unsaturated alkyl radical, the sum of the carbon atoms of R' and R being between 5 and 42.

* * * * *